(12) United States Patent
Preston et al.

(10) Patent No.: US 7,110,810 B2
(45) Date of Patent: Sep. 19, 2006

(54) THERAPEUTIC DEVICE FOR HANDS AND WRISTS

(75) Inventors: Andrea P. Preston, Miami, FL (US); Ivan G. Yaeger, Miami, FL (US)

(73) Assignee: Y.I.P. Corporation, Miami, FL (US)

( * ) Notice: Subject to any disclaimer, the term of this patent is extended or adjusted under 35 U.S.C. 154(b) by 36 days.

(21) Appl. No.: 10/831,555

(22) Filed: Apr. 26, 2004

(65) Prior Publication Data
US 2005/0240230 A1 Oct. 27, 2005

(51) Int. Cl.
*A61N 1/26* (2006.01)
*A61F 7/00* (2006.01)
*A61H 1/00* (2006.01)

(52) U.S. Cl. .......................... 607/3; 607/96; 607/111; 601/15; 601/46

(58) Field of Classification Search ............... 607/1, 607/2, 3, 96, 111, 27, 32, 41; 601/15, 46, 601/70, 40, 72, 80, 133, 136
See application file for complete search history.

(56) References Cited

U.S. PATENT DOCUMENTS

| | | | |
|---|---|---|---|
| 3,830,232 A | 8/1974 | McNair | 601/64 |
| 4,014,325 A | 3/1977 | Clarke | 601/121 |
| 4,020,856 A | 5/1977 | Masterson | 132/74.5 |
| 4,057,053 A | 11/1977 | Kunz | 601/27 |
| 4,198,962 A | 4/1980 | McCauley | 601/63 |
| 4,307,738 A | 12/1981 | Barns | 132/74.5 |
| 5,158,076 A * | 10/1992 | Thomsen | 601/156 |
| 5,868,689 A | 2/1999 | Faroky et al. | 601/120 |
| 2004/0082886 A1 * | 4/2004 | Timpson | 601/15 |

* cited by examiner

*Primary Examiner*—Robert E. Pezzuto
*Assistant Examiner*—Tammie K. Heller

(57) ABSTRACT

A therapeutic device for massaging hands and wrists which has upper and lower panels affixed to respective upper and lower housing via a plurality of compressible vibration-absorbing mounting pads. An elevated wrist rest extends across the anterior end of the outer face of the lower panel. The device includes a plurality of vibration mechanisms and heating/electrical stimulation elements mounted onto the outer fact of the upper and lower panels. A hinge connects the upper housing to the lower housing. A latch-and-switch mechanism engages and secures the upper and lower housing together and connects the electrical circuit of the upper housing with the electrical circuit of the lower housing. A plurality of batteries and a removable power cord are both interconnected with the device's electrical circuits to provide either battery or line voltage electrical power.

3 Claims, 3 Drawing Sheets

THERAPEUTIC DEVICE FOR HANDS AND WRISTS

CROSS-REFERENCE TO RELATED APPLICATIONS

This application is preceded by provisional patents 60/464,165 (filed Apr. 21, 2003) which embodies the present design, and 60/366,170 (filed Apr. 15, 2002) which embodies an earlier design.

STATEMENT REGARDING FEDERALLY SPONSORED RESEARCH OR DEVELOPMENT

Not Applicable

REFERENCE TO SEQUENCE LISTING, A TABLE OR A COMPUTER LISTING COMPACT DISK APPENDIX

Not Applicable

BACKGROUND OF THE INVENTION

This invention is related to devices that provide therapeutic massage of the hands and wrists. Past inventions have demonstrated massaging devices for hands or feet, with the majority of the electrically powered devices being designed for the lower extremities. McNair U.S. Pat. No. 3,942,520, and McCauley U.S. Pat. No. 4,198,962 disclose typical embodiments of foot massagers proving vibration and dry or liquid heat. Barns U.S. Pat. No. 4,307,738 shows a premanicure vibrating hand bath, while Masterson U.S. Pat. No. 4,020,856 shows a fingernail/hand cleaning device. None of these references show a device that provides massage, thermal and electrical stimulation therapy to the hands and wrists.

BRIEF SUMMARY OF THE INVENTION

The invention disclosed herein can be used in the home, workplace or clinical setting to relieve hands and wrists of fatigue. It can also promote healing of hand and wrist injuries through the use of electrical stimulation and thermal therapy. This device provides the following advantages not presented in prior art:
  Massages palms, fingers, wrists and back of hands simultaneously;
  Provides dry heat therapy;
  Provides electrical stimulation therapy;
  Operates on either battery or line voltage;
  Provides removable thermal gel packets for added comfort and thermal treatment;
  Provides a hand rest surface with adjustable elevation and firmness.

This device can provide all or any combination of the above features as required by the user.

DETAILED DESCRIPTION OF THE INVENTION

Figure 2:
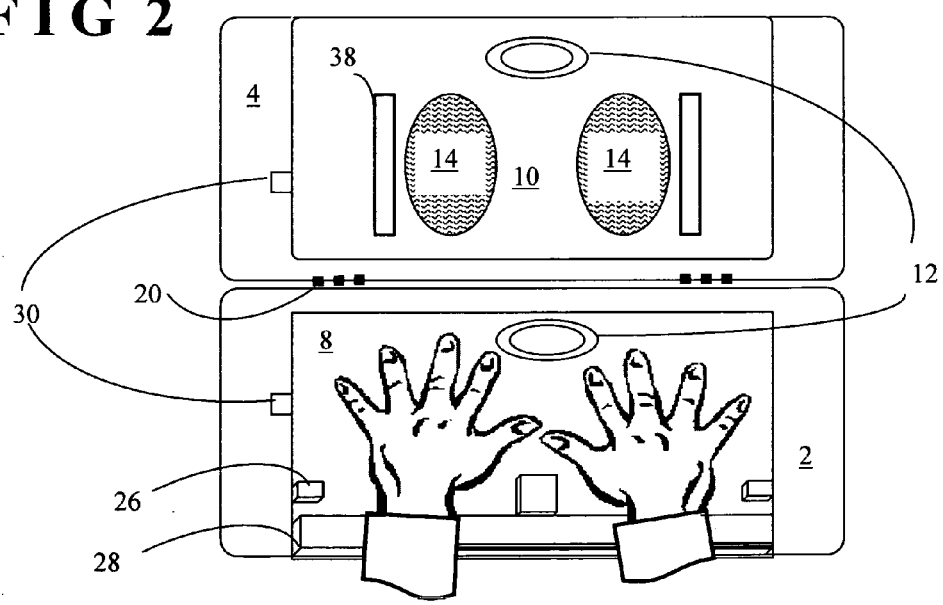
FIG. 2 depicts an overhead view of the device in the open position while in use without thermal gel packets.
Figure 3:
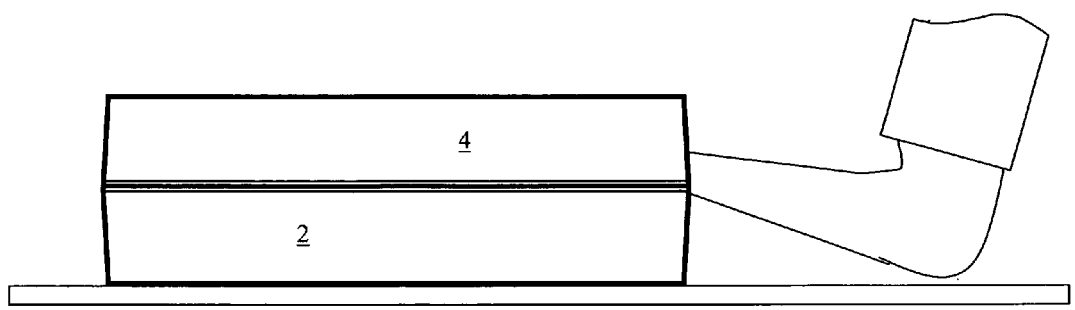
FIG. 3 depicts a side view of the device while being used in the closed position.
Figure 4:
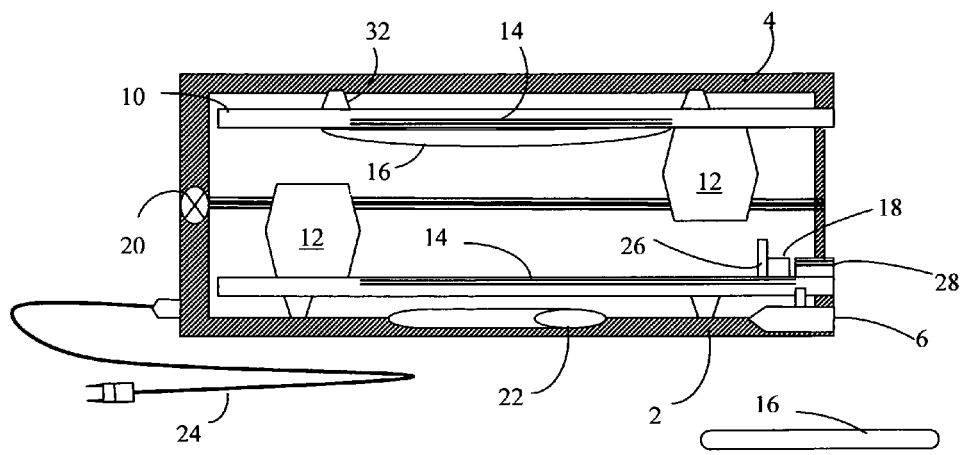
FIG. 4 depicts a cross sectional side view of the device in the closed position.
Figure 5:
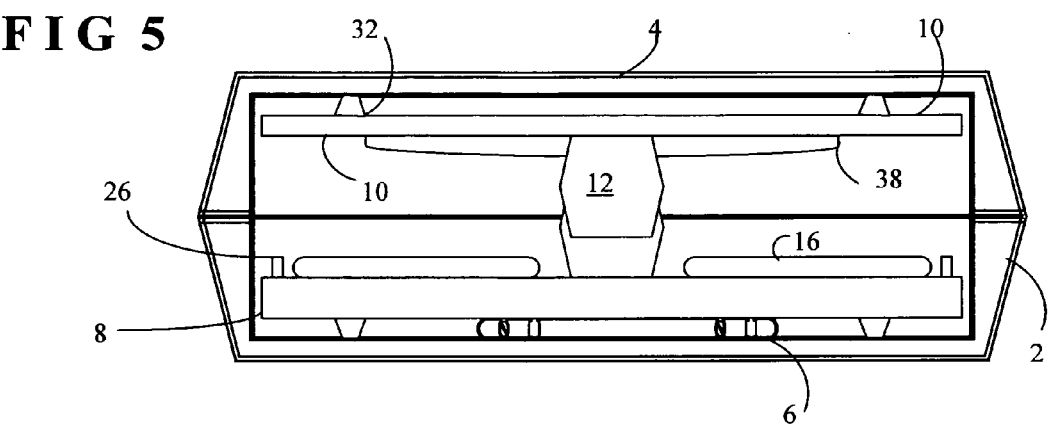
FIG. 5 depicts a frontal view of the device in the closed position.
Figure 6:
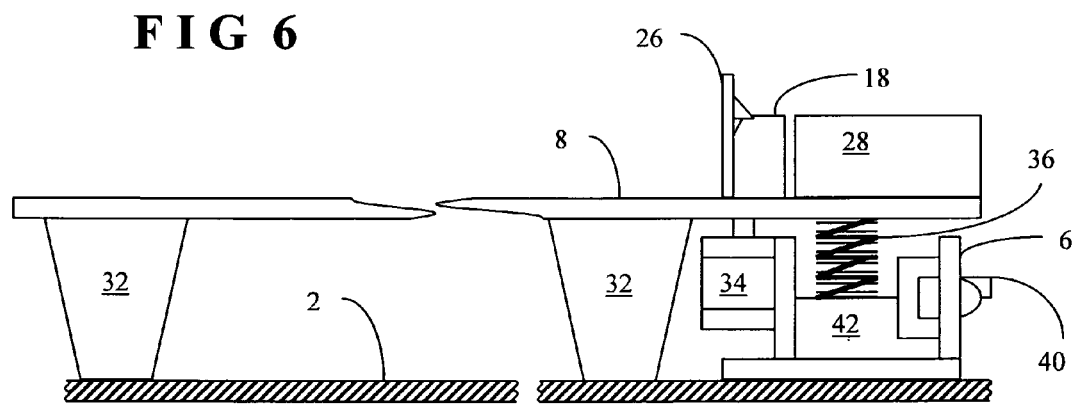
FIG. 6 depicts a side view of the internal mechanisms within lower housing 2.

The description presented herein and illustrated by FIGS. 1 through 6 pertains to the invention currently referred to as a "Therapeutic Device for Hands and Wrists". This device relieves fatigue and pain to hands and wrists caused by repetitive manual tasks (such as Carpal Tunnel Syndrome) and can be used in home and clinical settings. FIG. 4 shows a cutaway side view of this device with internal components depicted as follows. The outer housing of this device is comprised of lower housing 2 and upper housing 4 that are connected via hinge 20. Lower panel 8 is mounted within lower housing 2 via compressible, vibration absorbing mounting pads 32. Mounted onto the exposed face of lower panel 8 is vibrator mechanism 12, wrist rest 28, heating and electrical stimulation elements 14 and retainer bar clips 26. Thermal gel packets 16 fit over heating/electrical stimulation elements 14. Retainer bar 18 fits into retainer bar clips 26. Control panel 6, mounted in lower front edge of lower housing 2, features function switches and indicators 40. Spring 36 and activation switch 34 are mounted behind control panel 6 between upper panel 10 and the floor of lower housing 2 (as shown in FIG. 6). Control unit 42 contains timer and electrical pulse circuits. Lower portion of latch and switch mechanism 30 is mounted within lower housing 2 alongside lower panel 8. Batteries 22 are mounted within lower housing 10; optional power cord 24 can be plugged into lower housing 2 as an alternative power source. Upper panel 10 is mounted within upper housing 4 via mounting pads 32. Mounted onto the exposed face of upper panel 10 is vibrator mechanism 12 and thermal gel packet 16. Although not shown, heating/electrical stimulation elements 14 can also be fitted to upper panel 10. The upper portion of latch and switch mechanism 30 is mounted within upper housing 4 alongside upper panel 10. Upper and lower portions of latch and switch 30 are positioned to contact each other when upper housing 4 is closed against lower housing 2.

Figure 1:
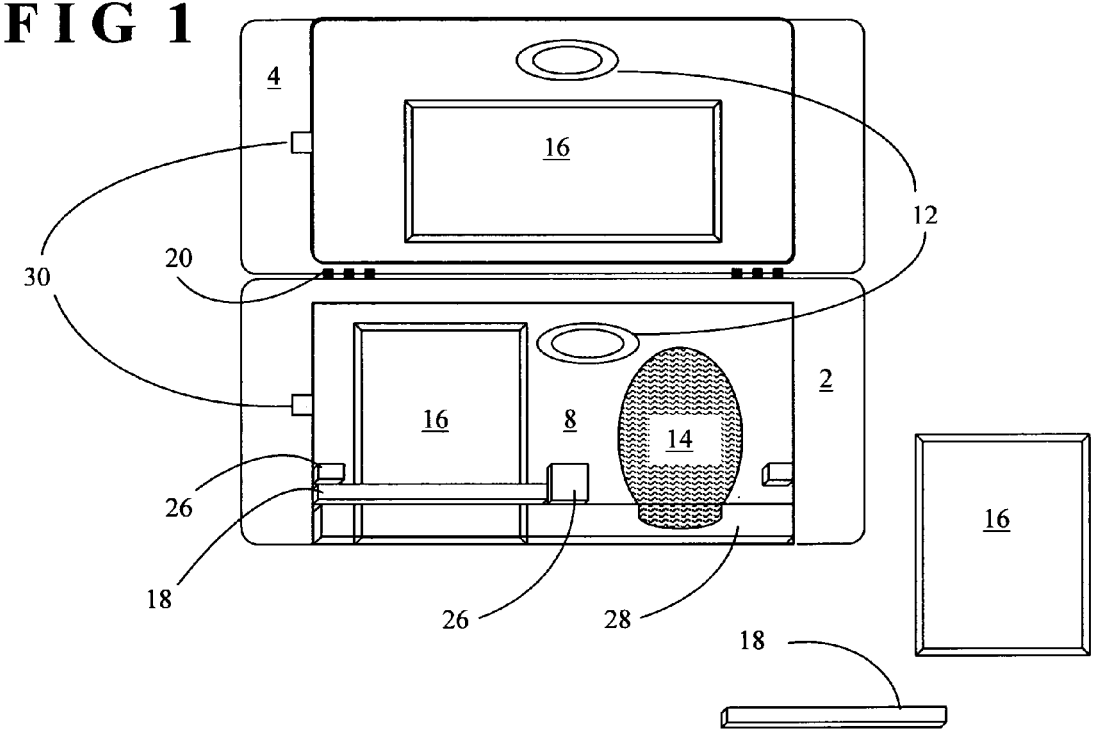
FIG. 1 depicts an overhead view of the device in the open position.

FIGS. 1, 2 and 3 show overhead and side views of this device while in use. To use this device, vibration, heat and electrical stimulation settings are activated via control panel 6. Control unit 42 provides electrical impulses to hands and wrists via electrical and heat therapy elements 14 for muscle stimulation therapy. Electrical power also causes vibrator mechanisms to transmit vibrations through hand rest 8 thereby creating a massaging action, while the heating portion of heating/electrical stimulation elements 14 to generate heat. Electrical power for the entire unit can be provided by batteries 22 mounted within lower housing 2, or by line voltage via power cord 24 (as shown in FIG. 4).

For full inner and outer hand therapy, upper housing 4 is closed and held mechanically and electrically interconnected via magnetic latching and switch 30 against lower housing 2. The user's hands and wrists are placed between hand rest 8 and upper panel 10. Hand pressure on hand rest 8 compresses mounting pads 32 and spring 36 until activation switch 34 is contacted. Vibration and heat are directed into the palms, wrists, fingers and back of hand. Removal of hands from lower panel 8 allows spring 36 and mounting pads 32 to lift said panel until actuation switch 34 is deactivated. Therapy session can also be ended when timer circuit of control unit 42 reaches the end of user-selected timed duration. To provide therapy to the palms or inner wrist only, upper housing 4 is lifted to the open position via hinge 20. This separates the upper and lower portions of latch and switch mechanism 30, thereby deactivating vibrator mechanism 12 and heating/electrical stimulation element 14 that are mounted onto upper panel 10.

Lower panel 8 also features removable thermal gel packets 16, consisting of sealed plastic envelopes filled with temperature-retaining gel. Each of said gel packets can be placed on the lower panel 8, with retainer bars 18 installed across the gel packet and engaged with retainer bar clips 26. In addition to holding gel packets in place against wrist rest 28 and lower panel 8, retainer bars 18 provide a variable hand support means. By varying the distribution of gel trapped on either side of the retainer bar 18, the user can adjust the supporting elevation and tension under the palm and wrist. Thermal gel packets 16 can transmit heat from heating/electrical stimulation elements 14, and provide a form-fitting cushion under the hand and wrist when used without retainer bars 18. Said gel packets can also be refrigerated or heated in hot water or a microwave oven prior to installation to provide an even greater level of thermal therapy. Thermal gel packet 16 is held onto upper panel 10 with semi-permanent attachment means 38 such as VEL-CRO®, or can be mounted permanently with brackets or other means.

We claim:

1. A therapeutic device for hands and wrists capable of providing massage, thermal, and electrical stimulation therapy comprising:
    a) a lower housing, which contains a lower panel of sufficient size to support the user's hands affixed onto said lower housing's inner surface via a plurality of compressible vibration-absorbing mounting pads, whereby said lower panel can be depressed downward into said lower housing;
    b) an upper housing, which contains an upper panel affixed onto said upper housing's inner surface via a plurality of compressible vibration-absorbing mounting pads, whereby said upper panel can be depressed upward into said upper housing;
    c) an elevated wrist rest extending across the anterior end of the outer face of the lower panel;
    d) a plurality of vibration mechanisms and heating/electrical stimulation elements mounted onto an outer face of the upper panel and the lower panel;
    e) a hinge which connects the upper housing to the lower housing, thereby allowing said upper housing to rest atop of said lower housing or pivot upwardly in clamshell fashion;
    f) a latch-and-switch mechanism mounted within side walls of the lower housing and the upper housing which can engage and secure said upper and lower housings together, and connect an electrical circuit of the upper housing with an electrical circuit of the lower housing; and
    g) a plurality of batteries mounted within the lower housing and a removable power cord extending through an aperture in said lower housing, which are both interconnected with the electrical circuits of the upper and lower housings to provide either battery of line voltage electrical power.

2. A therapeutic device as described in claim 1, which features a plurality of temperature retaining thermal gel capsules mounted onto the outer face of the lower panel and the upper panel via:
    a) removable retainer bars of the lower panel which rest longitudinally against the elevated wrist rest and are retained at both ends by clips, which allows the thermal gel capsule to be clamped between said retainer bar, the lower panel and the wrist rest, and the distribution of gel within said capsule to be varied; and
    b) a semi-permanent attachment means on the upper panel such as hook and loop attachment means, screws or hooks which secure the thermal gel capsule onto said upper panel.

3. A therapeutic device as described in claim 1 that includes an electrical control unit that provides a timer and electrical impulse generating means, which is mounted onto the inner surface of the lower housing and positioned directly under the wrist rest area of the lower panel and features:
    a) an activation switch which has an upwardly-extending activation button that rests against the inner face of the lower panel, whereby activation of therapy functions commence when the weight of the user's hand depresses said lower panel onto the activation button of said switch;
    b) a spring that extends upward and rests against the inner face of the lower panel, which assists the lower panel in returning to its original position and breaking contact with the activation switch when the user's hand is removed from said lower panel; and
    c) a control panel which faces the front edge of the lower housing and contains function switches and indicators for controlling and monitoring the therapy functions of the device.

* * * * *